United States Patent [19]

Lin et al.

[11] Patent Number: 5,099,010

[45] Date of Patent: Mar. 24, 1992

[54] INTERMEDIATES IN THE PREPARATION OF 3'-AMINO-2',3'-DIDEOXYCYTIDINE AND THE PHARMACOLOGICALLY ACCEPTABLE SALTS THEREOF

[75] Inventors: Tai-Shun Lin, North Haven; William H. Prusoff, Branford, both of Conn.

[73] Assignee: Research Corporation, New York, N.Y.

[21] Appl. No.: 864,645

[22] Filed: May 15, 1986

Related U.S. Application Data

[62] Division of Ser. No. 458,335, Jan. 17, 1983, Pat. No. 4,604,382.

[51] Int. Cl.$^5$ ............................................ C07H 17/00
[52] U.S. Cl. ...................................................... 536/23
[58] Field of Search .......................................... 536/23

[56] References Cited

U.S. PATENT DOCUMENTS 3,817,980  6/1974  Vorbruggen ......................... 536/23

OTHER PUBLICATIONS

Imazawa et al., J. Org. Chem., vol. 43, No. 15, pp. 3044–3048 1978.

*Primary Examiner*—John W. Rollins
*Attorney, Agent, or Firm*—Scully, Scott, Murphy & Presser

[57] ABSTRACT

This disclosure describes the preparation of 3'-amino-2', 3'-dideoxyctidine and the pharmacologically acceptable salts thereof which are useful in inhibiting the growth of transplanted tumors in mammals.

3 Claims, No Drawings

INTERMEDIATES IN THE PREPARATION OF 3'-AMINO-2',3'-DIDEOXYCYTIDINE AND THE PHARMACOLOGICALLY ACCEPTABLE SALTS THEREOF

The invention described herein was made in the course of work under a grant or award sponsored in part by the National Institutes of Health.

This is a divisional of copending application Ser. No. 458,335, filed on Jan. 17, 1983, now U.S. Pat. No. 4,604,382.

BRIEF SUMMARY OF THE INVENTION

This invention relates to 3'-amino-2',3'-dideoxycytidine of the formula

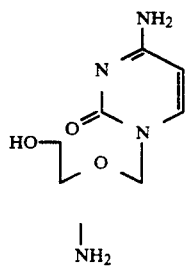

and the non-toxic pharmacologically acceptable acid addition salts thereof.

DETAILED DESCRIPTION OF THE INVENTION

The new compound has excellent water solubility (~0.5 g/mL at 23° C.) and readily forms non-toxic acid addition salts with a variety of pharmacologically acceptable organic and inorganic salt-forming reagents. Thus, acid addition salts formed by admixture of the organic free base with up to two equivalents of an acid, suitably in a neutral solvent, are formed with such acids as sulfuric, phosphoric, hydrochloric, hydrobromic, sulfamic, citric, lactic, malic, succinic, tartaric, acetic, benzoic, gluconic, ascorbic, and the like. For purposes of this invention, the free base is equivalent to the non-toxic acid addition salts. The acid addition salts are, in general, crystalline solids, very soluble in water, relatively soluble in methanol and ethanol but relatively insoluble in non-polar organic solvents such as diethyl ether, benzene, toluene, and the like.

The novel compound of the present invention may be readily prepared in accordance with the following reaction scheme:

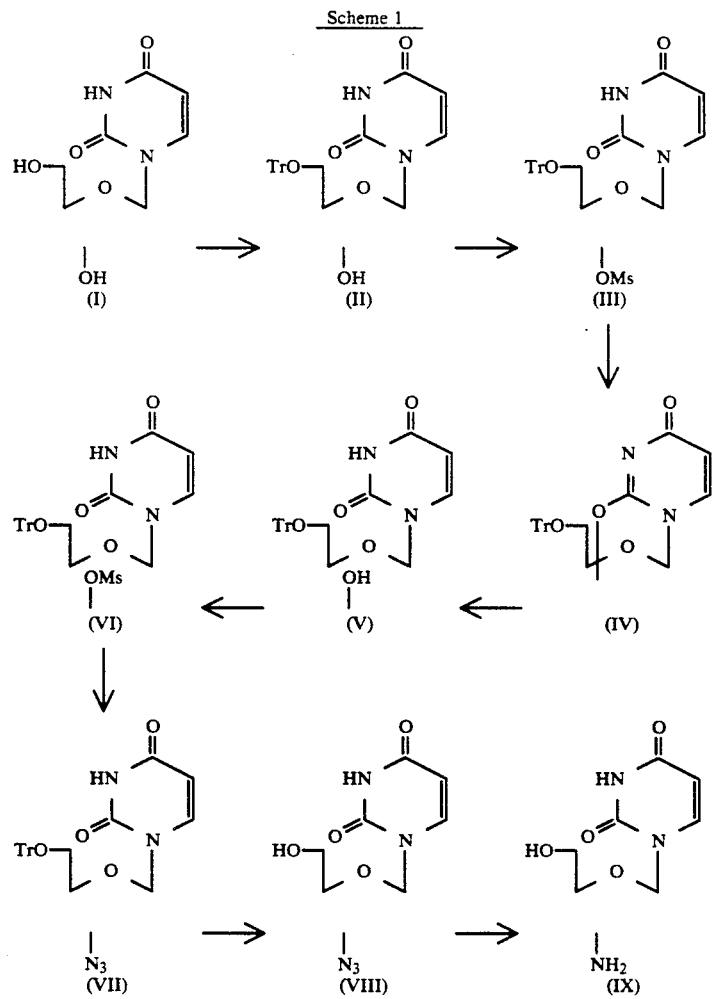

Scheme 2

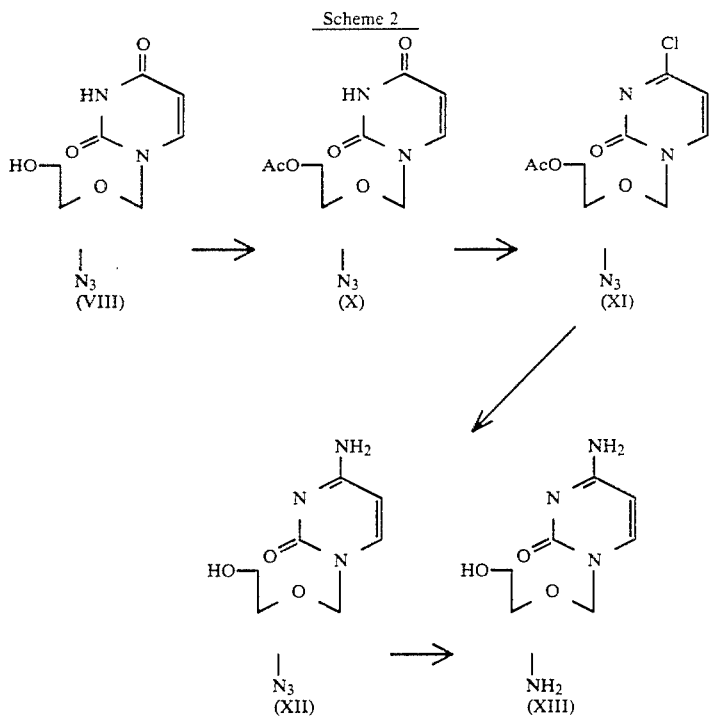

The synthesis of several new 3'-azido and 3'-amino nucleosides is outlined above. Tritylation of 2'-deoxyuridine (I) with trityl chloride in pyridine gives the corresponding 5'-O-trityl derivative, (II), which is then converted to the 3'-O-methanesulfonyl analog, (III), with methanesulfonyl chloride in pyridine. The replacement of the mesyloxy group at the 3'-position in (III) with net inversion to yield 1-(2'-deoxy-5'-O-trityl-β-D-lyxosyl)uracil (V), is accomplished by refluxing compound (III) with excess sodium hydroxide solution. Mesylation of compound (V) affords the sulfonate (VI). This compound is then treated with lithium azide in N,N-dimethylformamide followed by detritylation by o refluxing with 80% aqueous acetic acid to yield 3'-azido-2,3'-dideoxyuridine (VIII). Catalytic hydrogenation of compound (VIII) in the presence of 10% palladium on charcoal in ethanol gives 3'-amino-2',3'-dideoxyuridine (IX). Acetylation of compound (VIII) with acetic anhydride in pyridine at 4° C. yields 5'-O-acetyl-3'-azido-2',3'-dideoxyuridine (X). Reaction of compound (X) with thionyl chloride and N,N-dimethylformamide in absolute chloroform at reflux temperature for 6 hours affords the corresponding 4-chloro derivative (XI) which is then converted to 3'-azido-2',3'-dideoxycytidine (XII) by treatment with saturated methanolic ammonia at room temperature for 6 days. Hydrogenation of compound (XII) using 10% palladium on charcoal as a catalyst gives 3'-amino-2',3'-dideoxycytidine (XIII). Compounds (VIII) and (IX) are key intermediates for the synthesis of various 5-substituted 3'-azido and 3'-amino nucleoside analogs.

An alternate synthesis of compound (XIII) involves treatment of 3'-azido-5'-O-acetyl-2',3'-dideoxyuridine (X) with 4-chlorophenylphosphorodichloridate and 1,2,4-triazole in pyridine at room temperature for 3 days to give the 4-trizolylpyrimidinone derivative. Subsequent treatment with aqueous ammonia in dioxane (1:3 v/v) for 4 hours, then saturated methanolic ammonia overnight at room temperature, yields the 3'-azido analog (XII) Compound (XII) is then reduced under 50 psi of hydrogen in the presence of 10% palladium on charcoal at room temperature for 6 hours to obtain the desired 3'amino-2',3'-dideoxycytidine derivative (XIII).

The novel compound of this invention possesses the property of inhibiting the growth of transplanted mouse tumors as established by the following tests.

Lymphocytic leukemia L1210 and S-180 test procedure

Mouse L1210 and S-180 cells were maintained as suspension cultures in Fischer's medium supplemented with 10% horse serum at 37° C. in a humidified atmosphere of 5% $CO_2$-95% air. Under these conditions the generation time for L1210 and S-180 cells is approximately 12 and 18 hours, respectively. The test compound at the given concentration, was added to L1210 and S-180 cells ($2 \times 10^4$ cells/mL) which were in their exponential phase of growth. The increase in cell number of the drug-free culture (control), as well as that of the cultures supplemented with the test compound, was determined after 24, 48 and 72 hours of growth.

Transplantation of L1210 ascites cells was carried out by withdrawing peritoneal fluid from donor $CDF_1$ mice bearing 7-day growths. The suspension was centrifuged for 2 minutes (1600 g), the supernatant peritoneal fluid was decanted, and a 10-fold dilution with isotonic saline was made. The cell number was determined with a Coulter particle counter and the cell population was adjusted to $10^6$ cells/mL. One-tenth mL of the resulting cell suspension (containing approximately $10^5$ cells) was injected intraperitoneally into each animal. The drug was administered by intraperitoneal injection, beginning 24 hours after tumor implantation, twice daily for 3 consecutive days. The test compound was injected as a solution in isotonic saline. The drug was administered intraperitoneally in a volume of 0.25 mL. For any one experiment, animals were distributed into groups of four mice of comparable weight and maintained throughout the course of the experiment on a suitable diet and water "ad libitum". Controls given injections of a comparable volume of vehicle were included in each experiment. Mice were weighed during the course of the experiments, and the percentage change in body weight from onset to termination of therapy was used as an indication of drug toxicity. Determination of the sensitivity of ascitic neoplasms to this agent were based on the prolongation of survival time afforded by the drug treatments. The median survival time and the ratio of survival time for treated (T)/control (C) was calculated.

3'-Amino-2',3'-dideoxycytidine was screened against CDF1 female mice bearing L1210 leukemia according to the above protocol. Three groups of mice with 4 mice in each group were inoculated with $1 \times 10^5$ L1210 murine leukemia cells. Starting 24 hours post inoculation, the first group of mice was injected with saline as the vehicle control, the second group with 160 mg/kg of the test compound in saline twice a day, for 3 days. All control mice died by day 9. In the group treated with the test compound, one mouse died at day 21, the second at day 24, the third at day 29 and the last one at day 31, yielding a T/C×100 value of 283. This data shows that the compound of this invention exhibits significant anticancer activity against L1210 leukemia in vivo.

3'-Amino-2',3'-dideoxycytidine was also screened against S-180 neoplastic cells in vitro. The $ID_{50}$ values were estimated from dose-response curves compiled from at least two independent experiments and represent the drug concentration required to inhibit replication of L1210 or S-180 neoplastic cells by 50%. The results are shown in the table below.

TABLE

|  | $ID_{50}$ ($\mu M$) | |
|---|---|---|
|  | L1210 | S-180 |
| 3'-amino-2',3'-dideoxycytidine | 0.7 | 4 |

$ID_{50}$ values were determined from plots of mean cell counts after 72 hours. Assays were carried out in triplicate with appropriate controls.

Thus, 3'-amino-2',3'-dideoxycytidine has shown potent anticancer activity against both L1210 and S-180 cells in vitro ($ID_{50}$ 0.7 and 4 $\mu M$, respectively).

More significantly, the cytotoxicity of the novel compound was found to be uniquely prevented by 2'-deoxycytidine and not by other pyrimidine deoxyribo- and ribonucleosides. The preventive effect of 2'-deoxycytidine on the cytotoxicity of the novel compound against L1210 cells was dose dependent. At a 5 $\mu M$ concentration of this compound the addition of 25 $\mu M$ and 100 $\mu M$ of 2'-deoxycytidine prevented the cytotoxicity of the novel compound against L1210 cells by 35% and 100% respectively. However, the addition of 25 $\mu M$ of 2'-deoxycytidine to 20 $\mu M$ of the new compound prevented the cytotoxicity of this compound against S-180 cells by 27%.

The active ingredient of the therapeutic compositions and the novel compound of the present invention inhibit transplanted mouse tumor growth and induce regression and/or palliation of leukemia and related cancers in mammals when administered in amounts ranging from about 5 mg to about 30 mg per kilogram of body weight per day, and such dosage units are employed that a total of from about 350 mg to about 2.1 grams of the active compound for a subject of about 70 kg of body weight are administered in a 24-hour period. This dosage regimen may be adjusted to provide the optimum therapeutic response. For example, several divided doses may be administered daily or the dose may be proportionally reduced as indicated by the exigencies of the therapeutic situation. A decided practical advantage is that the active compound may be administered in any convenient manner such as by the oral, intravenous, intramuscular, or subcutaneous routes.

The active compound may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like Such compositions and preparations should contain at least 0.1% of active compound. The percentage of the compositions and preparations may, of course, be varied and may conveniently be between about 2 to about 60% of the weight of the unit. The amount of active compound in such therapeutically useful compositions is such that a suitable dosage will be obtained Preferred compositions or preparations according to the present invention are prepared so that an oral dosage unit form contains between about 50 mg and 300 mg of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed In addition, the active compound may be incorporated into sustained-release preparations and formulations.

The active compound may also be administered parenterally or intraperitoneally. Solutions of the active compound as a free base or pharmacologically acceptable salt can be prepared in water suitably mixed with a surfactant such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporanous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of micro-organisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatable with the active ingredient, its use in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

Regression and palliation of cancers are attained, for example, using intraperitoneal administration. A single intravenous dosage or repeated daily dosages can be administered. Daily dosages up to about 5 or 10 days are often sufficient. It is also possible to dispense one daily dosage or one dose on alternate or less frequent days. As can be seen from the dosage regimens, the amount of principal active ingredient administered is a sufficient amount to aid regression and palliation of the leukemia or the like, in the absence of excessive deleterious side effects of a cytotoxic nature to the hosts harboring the cancer. As used herein, cancer disease means blood malignancies such as leukemia, as well as other solid and non-solid malignancies such as the melanocarcinomas, lung carcinomas, and mammary tumors. By regression and palliation is meant arresting or retarding the growth of the tumor or other manifestation of the disease compared to the course of the disease in the absence of treatment.

This invention will be described in greater detail in conjunction with the following specific examples.

EXAMPLE 1

5'-O-Trityl-2'-deoxyur-idine (II)

A mixture of 2'-deoxyuridine (100 g, 0.44 mol) and triphenylmethyl choride (147 g, 0.53 mol) in 250 mL of pyridine was heated at 100° C. for 30 minutes. One-third of the cooled solution was added at a slow flow rate to a mixture of ice water (2:3) in a commercial blender blending for 3-5 minutes after adding the solution. The resulting white precipitate was filtered and washed twice, stirring in 2 L of water. Recrystallization was accomplished by refluxing the product in a benzene-acetone solution (1:1) for 15 minutes, yielding 128 g (62%). The compound softened at 76° C., began to melt at 152-155° C., and darkened in color at 155-159° C. $R_f = 0.71$ ($CHCl_3$—EtOH, 4:1).

EXAMPLE 2

3'-O-Methanesulfonyl-5'-O-trityl-2'-deoxyuridine (III)

The product of Example 1 (59 g, 0.13 mol) was dissolved at room temperature in 120 mL of pyridine. The solution was put into an ice bath and 29 mL of methanesulfonyl chloride (0.34 mol) was added dropwise. The resulting solution was allowed to stir at 4° C. for 24 hours. The reaction mixture was added in three portions at a slow flow rate into a blender as described previously. The pea-green solid was collected by filtration, washed twice with 2 L of water, and dried to yield 58 g (93%). The compound started to soften at 85° C. and melted at 106-108° C. $R_f = 0.62$ ($CHCl_3$—EtOH, 10:1). Anal. ($C_{29}H_{28}N_2O_7S$).

EXAMPLE 3

1-(2'-Deoxy-5'-O-trityl-β-D-lyxosyl)-uracil (V)

A solution of the compound of the preceding example (45 g, 0.08 mol) in 450 mL absolute EtOH, 150 mL 1 N NaOH, and 200 mL $H_2O$ was refluxed for 4 hours at 130° C. The solution was transferred to a 4 L beaker and diluted with about 500 mL of water and ice. While vigorously stirring, the solution was acidified to pH 3 with concentrated HCl. After stirring 20 minutes, the precipitate was filtered, washed in 4 L of water, filtered again and partially recrystallized in hot alcohol to yield 34 g (88%). $R_f = 0.55$ ($CHCl_3$—EtOH, 10:1).

EXAMPLE 4

1-(2'-Deoxy-3'-O-methanesulfonyl-5'-O-trityl-β-(D-lyxosyl)-uracil (VI)

The product of Example 3 (26 g, 0.054 mol) was dissolved in 100 mL of pyridine, then placed into an ice bath. Methanesulfonyl chloride (14.5 mL, 0.187 mol) was slowly added dropwise. After stirring at room temperature for 24 hours, the solution was blended in three portions as described in Example 1. The tan solid was collected by filtration, washed with 4 L of water, filtered and dried, to afford 26 g (91%). $R_f=0.84$ (CHCl$_3$—EtOH, 4:1).

EXAMPLE 5

3'-Azido-5'-O-trityl-2',3'-dideoxyuridine (VII)

A mixture containing the compound of the preceding example (26 g, 47.8 mmol) and lithium azide (7.0 g, 143 mmol) in 60 mL of DMF was heated at 85° C. for 2 hours. The solution was allowed to cool before adding, in two portions, to a blender containing ice water as described in Example 1. The filtered crystals were washed in 1 L of water, filtered and dried, to yield 22 g (86%). $R_f=0.59$ (CHCl$_3$—EtOH, 10:1). IR (KBr), 4.75 μ (azido).

EXAMPLE 6

3'-Azido-2',3'-dideoxyuridine (VIII)

A suspension of the compound of the preceding example (13 g, 26 mmol) in 50 mL of 80% acetic acid was refluxed at 110° C. for 20 minutes. The solution was permitted to slowly cool to room temperature, at which time some trityl alcohol precipitated out. 10 mL of water was added to aid in the precipitation and the mixture was filtered. The filtrate was clarified by stirring with charcoal for 20 minutes After filtering (twice), the filtrate was concentrated under reduced pressure (35° C.) until it yielded tan crystals. The product was filtered and the filtrate was continuously concentrated until it no longer produced the solid. After washing with EtOH, Et$_2$O, and drying in the oven, 4.6 g (70%) of the product was collected mp 161°–163° C. (dec); $R_f=0.18$ (CHCl$_3$—EtOH, 10:1); IR (KBr) 4.80 u (azido); UV (0.01 N HCl), $\lambda_{max}$ 260 nm ($\epsilon$10,760), $\lambda_{min}$ 232 nm; UV (0.01 N NaOH), $\lambda_{max}$ 260 nm ($\epsilon$8,470), $\lambda_{min}$ 240 nm; NMR (DMSO-d$_6$): δ1.81–2.06 (m, 2H, 2'-H), 2.96–3.19 (m, 2, 5'-H), 3.38–3.42 (m, 1, 4'-H), 3.91–3.97 (m, 1, 3'-H), 4.77 (t, 1, 5'-OH, D$_2$O exchangeable), 5 20 (d, 1, 5'-U), 5.63 (t, 1, 1'-H), 7.40 (d, 1, 6-H), 10.89 (broad s, 1, 3'NH, D$_2$O exchangeable). Anal. (C$_9$H$_{10}$N$_5$O$_4$). Calculated C, 45.69, H, 4.38, N, 27.66. Found C, 45.82, H, 4.57, N, 27.36.

EXAMPLE 7

3'-Amino-2',3'-dideoxyuridine (IX)

A solution of the compound of the preceding example (2.8 g, 10.9 mmol) in 150 mL of EtOH was hydrogenated under 50 psi for 2 hours in the presence of 10% palladium on charcoal (0.5 g). At the end of the reduction, norite was added to the mixture and stirred for 30 minutes. After filtration (twice), the filtrate was concentrated to a glass (35° C.). The residue was crystallized from EtOH-Et$_2$O to yield 2.1 g (86%) of a fine tan powder which softened around 156° C. and decomposed at 163° C. Ninhydrin test: positive. UV (0.01 N HCl), $\lambda_{max}$ 260 nm ($\epsilon$9,060), $\lambda_{min}$ 229 nm; UV (0.01 N NaOH), $\lambda_{max}$ 260 nm ($\epsilon$7,450), $\lambda_{min}$ 240 nm; NMR (DMSO-d$_6$): δ1.95–2.12 (m, 2H, 2'-H), 3.32–3.39 (m, 3, 4'-H, and 3'-NH$_2$, D$_2$O exchangeable), 3.52–3.65 (m, 3, 3'-H, and 5'-H), 4.8 (broad s, 1, 5'-OH, D$_2$O exchangeable), 5.59 (d, 1, 5-H), 6.05 (t, 1, 1'-H), 7.90 (d, 1, 6-H). Anal. (C$_9$H$_{13}$N$_3$O$_4$). Calculated C, 47.58, H, 5.77, N, 18.49. Found C, 47.38, H, 6.0, N, 18.20.

EXAMPLE 8

3'-Azido-5'-O-acetyl-2',3'-dideoxyuridine (X)

Acetic anhydride (19 mL, 0.20 mol) was added dropwise to a solution of the compound of Example 6 (5.0 g, 19.8 mmol) in 40 mL of pyridine at 0° C. After stirring at 4° C for 24 hours, the reaction mixture was quenched by slowly adding 15 mL of water (ice bath). The solvents were removed under reduced pressure (35° C.), leaving a thick syrup. This residue was then dissolved in 50 mL of CHCl$_3$ and washed with water (four times), saturated NaHCO$_3$ solution (twice), and water again (twice). The CHCl$_3$ solution was clarified with charcoal. After filtration, the solution was dried with anhydrous MgSO$_4$. Upon filtering, the filtrate was concentrated (35° C.) and dried under reduced pressure overnight to yield 4.2 g (71%) of crude product which was used for the next reaction without further purification. $R_f=0.68$ (CHCl$_3$—EtOH, 4:1). IR (film) 4.80 μ (azido).

EXAMPLE 9

5'-O-Acetyl-3'-azido-2',3'-dideoxy-4-chlorouridine (XI)

The glassy residue of the product of the preceding example (4.2 g, 14.0 mmol) was dissolved in 60 mL of absolute CHCl$_3$, to which 9.5 mL of thionyl chloride and 0.6 mL of dry DMF were added. The reaction mixture was stirred under reflux for 6 hours at 90° C., after which it was concentrated (35° C.) to dryness. This residue was co-evaporated (five times) with 80 mL portions of toluene. Following the final concentration, the residue was put under reduced pressure (40° C.) for 30 minutes. The product was used immediately for the next reaction.

EXAMPLE 10

3'-Azido-2',3'-dideoxycytidine (XII)

The product of the preceding example was dissolved in 100 mL of absolute MeOH saturated with NH$_3$ at 0° C. The solution was allowed to stir at room temperature in a pressure bottle for 6 days. After the elapsed time, the reaction mixture was cooled to 0° C. before opening. The solvent was evaporated (30° C.) under reduced pressure to yield a glassy residue which was dissolved in 150 mL of MeOH and clarified with charcoal. After filtering, the filtrate was reduced to a small volume. This concentrated solution was then applied directly to a column (3.5×94 cm) packed with EM Silica gel 60, using a MeOH-CHCl$_3$ (2:3) eluting solution. The desired fractions with an $R_f$ of 0.65 were collected and concentrated. The product was further purified on a Waters Prep LC/System 500A, with a 500/Silica cartridge, using a CHCl$_3$-MeOH (4:1) solvent system. The fractions ($R_f=0.65$) were collected and concentrated to about 50 mL and clarified with charcoal. After filtering, the solution was evaporated to yield 1.1 g (31%) of a yellow glass. The analytically pure sample was obtained by crystallization from EtOH-Et$_2$O. The compound softened at 92° C., effervesced around 140° C., and melted at 160–162° C. $R_f=0.65$ (MeOH-CHCl$_3$, 2:3), IR (film), 4.80 μ (azido); UV (0.01 N HCl), $\lambda_{max}$ 278 nm ($\epsilon$13,460), $\lambda_{min}$ 238 nm; UV (0.01 N NaOH), $\lambda_{max}$ 268 nm ($\epsilon$11,070), $\lambda_{min}$ 246 nm; NMR (DMSO-d$_6$): δ2.17–2.34 (m, 2, 2-H), 3.58–3.62 (m, 2, 5'-H), 3.82–3.86 (m, 1, 4'-H), 4.30–4.37 (m, 1, 3'-H), 5.17 (t, 1, 5'-OH, D$_2$O exchangeable), 5.72 (d, 1, 5-H), 6.97 (t, 1, 1'-H), 7.16 (broad d, 2, 4-NH$_2$, D$_2$O exchangeable), 7.78 (d, 1, 6-H). Anal. ($C_9H_{12}N_6O_3$). Calculated C, 42.86, H, 4.80, N, 33.32. Found C, 42.86, H, 4.78, N, 33.02.

EXAMPLE 11

3'-Amino-2',3'-dideoxycytidine (XIII)

A solution of the product of the preceding example (1.11 g, 4.40 mmol) in 100 mL of MeOH was hydrogenated under 50 psi for 2 hours in the presence of 10% palladium on charcoal (0.5 g). After filtration, the filtrate was concentrated to give a glassy residue. White crystals (0 65 g, 65%) were achieved by dissolving the residue in a minimal amount of MeOH, then slowly adding $CHCl_3$ and $Et_2O$. The compound began to darken in color at 184° C. until it melted at 207° C. Ninhydrin test: positive UV (0.01 N HCl), $\lambda_{max}$ 277 nm ($\epsilon$11,790), $\lambda_{min}$ 238 nm; UV 0.01 N NaOH), $\lambda_{max}$ 268 nm ($\epsilon$7,820), $\lambda_{min}$ 246 nm; NMR (DMSO-$d_6$): $\delta$1.90–2.08 (m, 2, 2'-H), 3.27–3.34 (m, 3, 4'-H, and 3'-$NH_2$, $D_2O$ exchangeable), 3.51–3.66 (m, 3, 3'-H, and 5'-H), 4.94 (broad s, 1, 5'-OH, $D_2O$ exchangeable), 5.69 (d, 1, 5-H), 6.04 (t, 1, 1'-H), 7.06 (broad d, 2, 4-NH , $D_2O$ exchangeable), 7.87 (d, 1, 6-H). Anal. ($C_9H_{14}N_4O_3$) Calculated C, 47.48, H, 6.24, N, 24.77. Found C, 47.49, H, 6.49, N, 24.70.

What is claimed is:

1. 3'-Azido-2',3'-dideoxyuridine.
2. 5'-O-Acetyl-3'-azido-2',3'-dideoxyuridine.
3. 3'-Azido-2',3'-dideoxycytidine.

* * * * *

UNITED STATES PATENT AND TRADEMARK OFFICE
CERTIFICATE OF CORRECTION

PATENT NO. : 5,099,010

DATED : March 24, 1992

INVENTOR(S) : Tai-Shun Lin, et al

It is certified that error appears in the above-identified patent and that said Letters Patent is hereby corrected as shown below:

In the Abstract, line 2: "dideoxyctidine" should read as --dideoxycytidine--

Column 3, line 42; delete "o"

Column 5, line 15: "CDF1" should read as --$CDF_1$--

Column 5, line 47: "($ID_{50}$0.7" should read as --($ID_{50}$ = 0.7--

Column 8, line 19: "doxyur-idine" should read as --deoxyuridine--

Column 9, line 35: "$Et_sO$" should read as --$Et_2O$--

Column 9, line 42: "5 20" should read as --5.20--

Column 9, line 44: "5'-U" should read as --5'-H)--.

UNITED STATES PATENT AND TRADEMARK OFFICE
CERTIFICATE OF CORRECTION

PATENT NO. : 5,099,010

DATED : March 24, 1992

INVENTOR(S) : Tai-Shun Lin, et al

It is certified that error appears in the above-identified patent and that said Letters Patent is hereby corrected as shown below:

Column 12, line 7: "4-NH" should read as --4-$NH_2$--

Signed and Sealed this

Tenth Day of August, 1993

Attest:

MICHAEL K. KIRK

Attesting Officer    Acting Commissioner of Patents and Trademarks